(12) United States Patent
Obinata et al.

(10) Patent No.: US 9,194,823 B2
(45) Date of Patent: Nov. 24, 2015

(54) RADIATION INSPECTION APPARATUS

(75) Inventors: Hirohiko Obinata, Tokyo (JP); Kumiko Horikoshi, Tokyo (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 942 days.

(21) Appl. No.: 13/406,312

(22) Filed: Feb. 27, 2012

(65) Prior Publication Data

US 2012/0221275 A1 Aug. 30, 2012

(30) Foreign Application Priority Data

Feb. 28, 2011 (JP) ................................ P2011-042240

(51) Int. Cl.
*G01N 23/16* (2006.01)
(52) U.S. Cl.
CPC ..................................... *G01N 23/16* (2013.01)
(58) Field of Classification Search
CPC ......... A61B 1/00; G01N 12/02; G01N 23/04; G01V 5/005; G01V 5/0016; G01V 5/0075; G01T 3/06
USPC ........ 250/358.1; 375/492.1; 378/4, 57, 62, 64
See application file for complete search history.

(56) References Cited

U.S. PATENT DOCUMENTS

| | | | |
|---|---|---|---|
| 5,877,494 A * | 3/1999 | Larsen et al. ................. | 250/234 |
| 8,447,012 B2 * | 5/2013 | Ichizawa et al. .............. | 378/113 |
| 2002/0185612 A1 * | 12/2002 | Chalmers et al. .......... | 250/492.1 |
| 2006/0058974 A1 * | 3/2006 | Lasiuk et al. .................... | 702/97 |
| 2007/0114428 A1 * | 5/2007 | Yoshino et al. .......... | 250/370.09 |
| 2008/0152081 A1 * | 6/2008 | Cason .............................. | 378/57 |
| 2010/0266097 A1 * | 10/2010 | Okunuki et al. ................... | 378/9 |
| 2011/0013748 A1 * | 1/2011 | Ichizawa et al. .............. | 378/113 |
| 2011/0147603 A1 * | 6/2011 | Ichizawa et al. .............. | 250/375 |
| 2012/0221275 A1 * | 8/2012 | Obinata et al. ................... | 702/97 |
| 2013/0038741 A1 * | 2/2013 | Kovalchuk .................... | 348/197 |

FOREIGN PATENT DOCUMENTS

| | | |
|---|---|---|
| JP | 5683333 A | 7/1981 |
| JP | 62-193505 U | 12/1987 |
| JP | 07-052573 A | 2/1995 |
| JP | 07-052573 Y2 | 11/1995 |
| JP | 11064246 A | 3/1999 |
| JP | 2011022030 A | 2/2011 |

* cited by examiner

*Primary Examiner* — John Breene
*Assistant Examiner* — Jeffrey Aiello
(74) *Attorney, Agent, or Firm* — Sughrue Mion, PLLC

(57) ABSTRACT

A radiation inspection apparatus may include a radiation source that irradiates linear radiation, which is parallel to an inspection direction set on an inspection target, to the inspection target, a line type detector that detects the radiation transmitted through the inspection target, a correction detector that is disposed in at least one of a position between the radiation source and the inspection target and a position between the inspection target and the line type detector, the correction detector moving along the inspection direction to detect the radiation, which has been irradiated from the radiation source, at each of a plurality of inspection positions along the inspection direction, and a correction device that corrects the detection result of the line type detector by using the detection result of the correction detector.

19 Claims, 9 Drawing Sheets

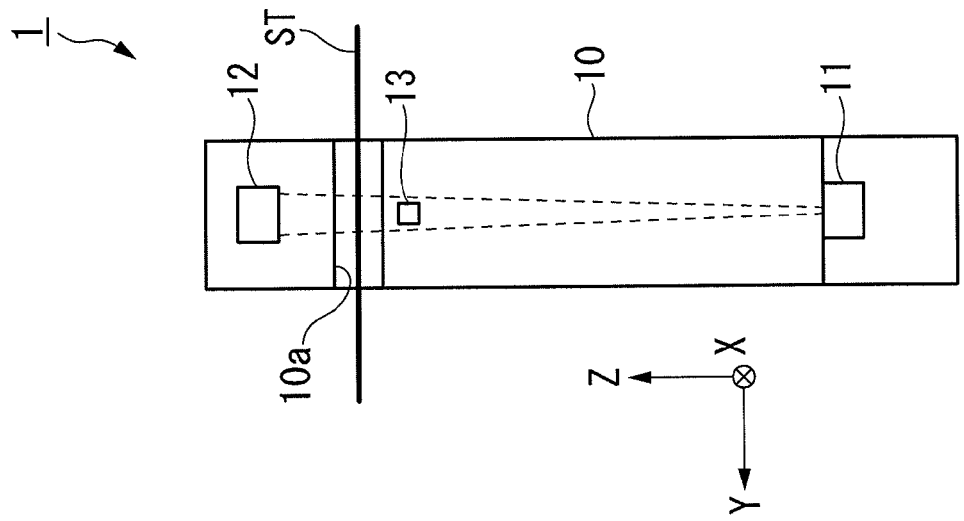
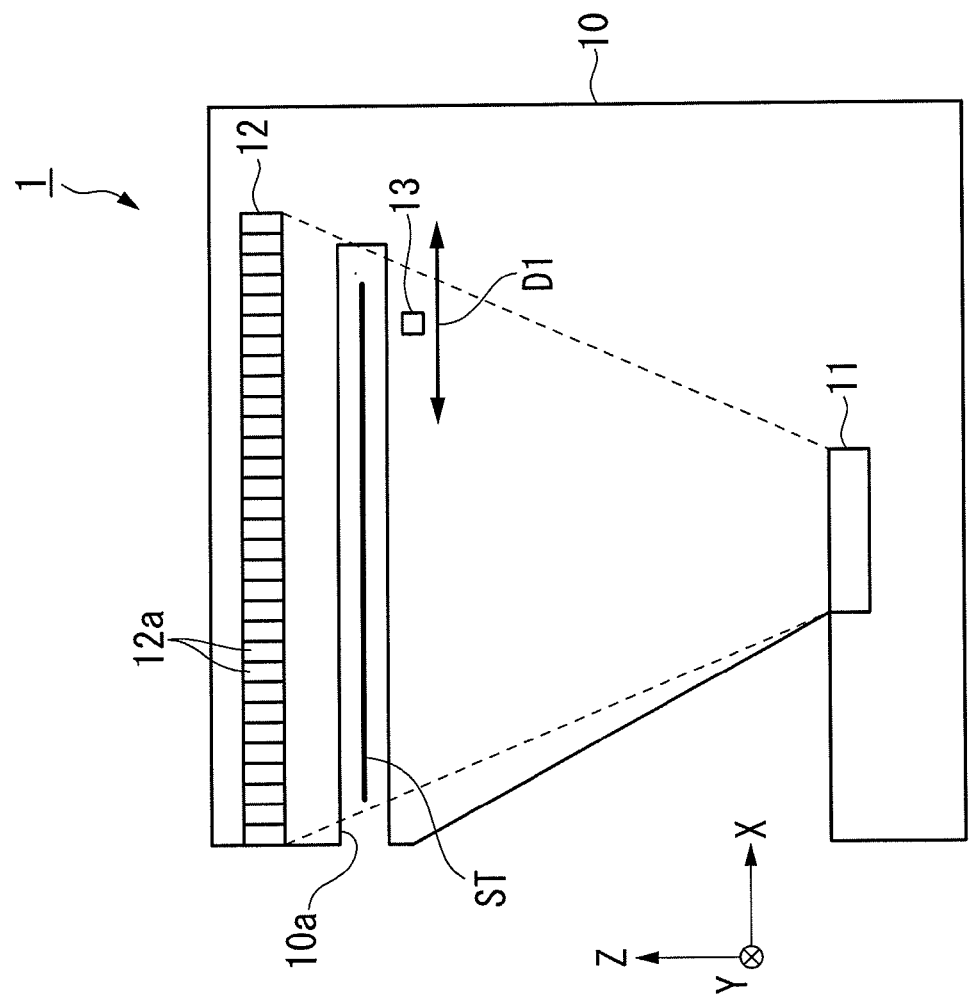

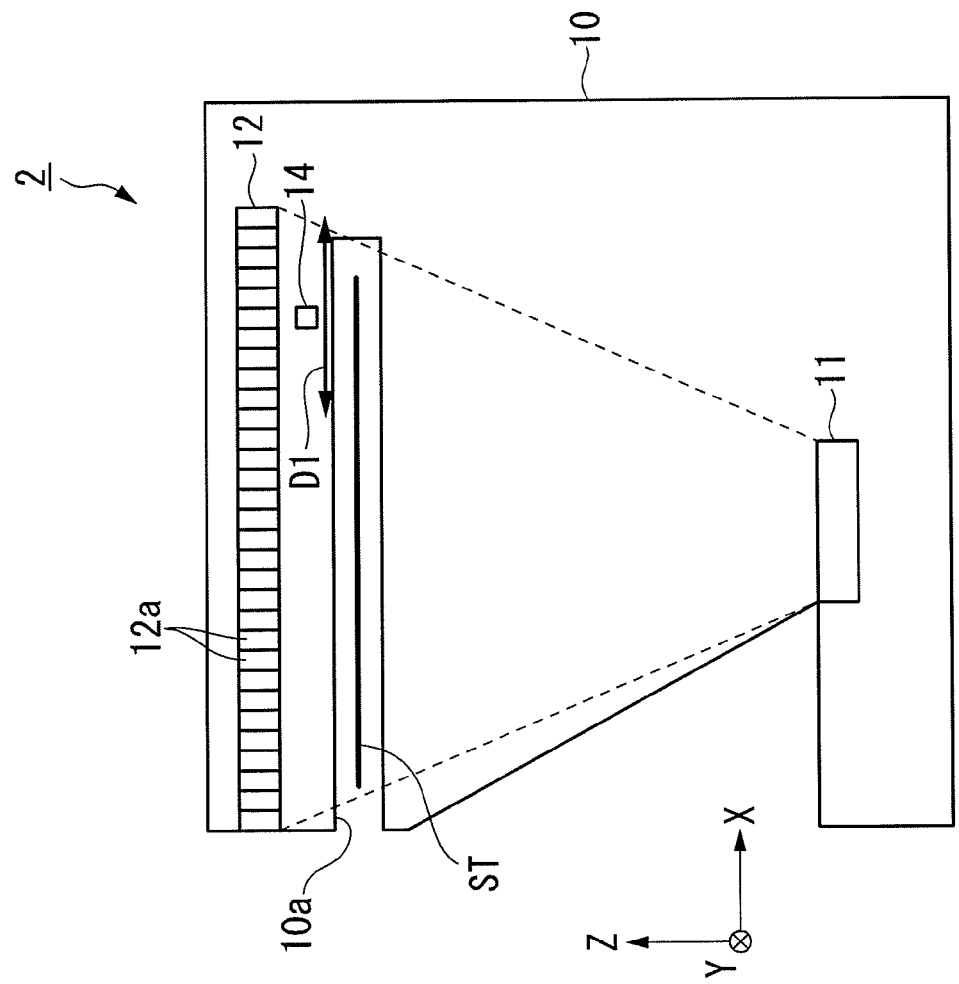
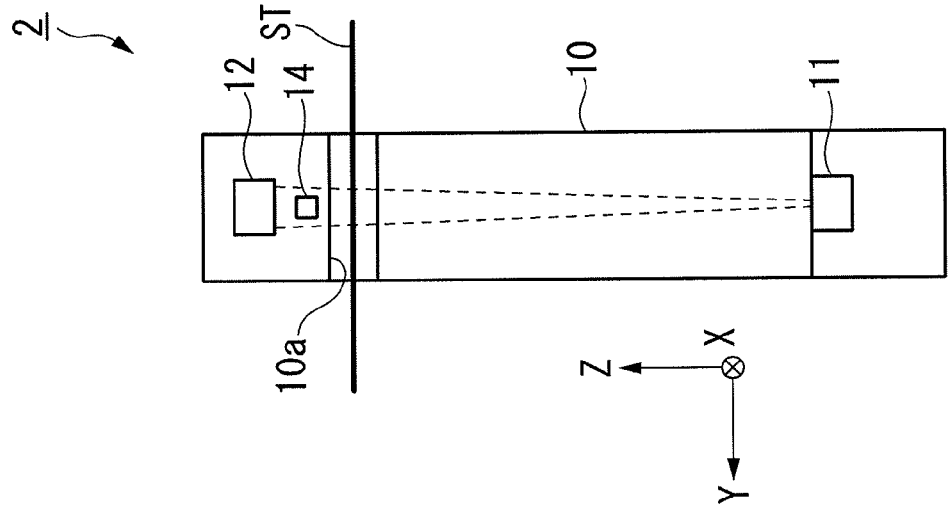

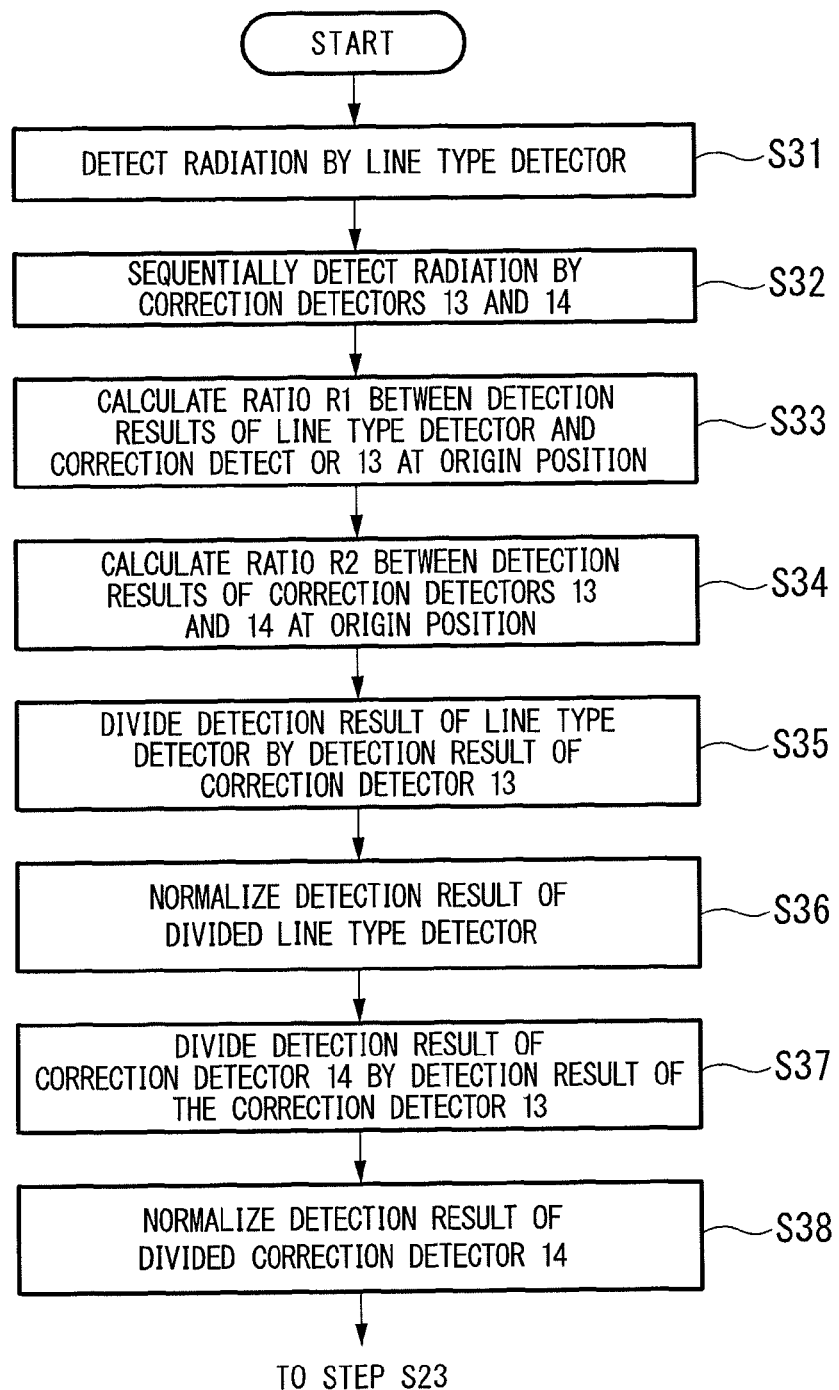

RADIATION INSPECTION APPARATUS

BACKGROUND OF THE INVENTION

1. Field of the Invention

The present invention relates to a radiation inspection apparatus that inspects an inspection target using radiation.

Priority is claimed on Japanese Patent Application No. 2011-042240, filed Feb. 28, 2011, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

A radiation inspection apparatus is an apparatus which inspects an inspection target by irradiating radiation (for example, electromagnetic waves with a wavelength of 10 micron or more, such as X-rays, $\beta$-rays, $\gamma$-rays, ultraviolet rays, visible rays, infrared rays, and radio waves) to the inspection target and detects the radiation transmitted through the inspection target so as to obtain permeation characteristics. The radiation inspection apparatus has been used in various fields due to the features by which characteristics of the inspection target may be inspected without damaging the inspection target. For example, in the field of production, the radiation inspection apparatus is often used as a thickness inspecting apparatus to inspect the thickness or the amount of coating of a produced sheet or film (a single-layer film and a multi-layer film) online.

Here, thickness inspecting apparatuses is broadly classified into "scanning type inspection apparatuses" and "whole surface inspection type inspection apparatuses." The former "scanning type inspection apparatus" is an apparatus that has, for example, a configuration in which a radiation source head generating radiation and a detector head such as an ionization chamber are disposed so as to face each other with an inspection target interposed therebetween and both heads are movable together in a reciprocating manner in a direction (the width direction of the inspection target) intersecting a direction in which the inspection target flows. In contrast, the latter "whole surface inspection type inspection apparatus" is an apparatus that has, for example, a configuration in which a radiation source head generating radiation extending in a line shape in the width direction of an inspection target and a detector head with a line type detector having a plurality of detection elements arranged in the width direction of the inspection target are disposed so as to be fixed with the inspection target interposed therebetween.

The "scanning type inspection apparatus" measures the distribution of the thickness of the inspection target in the width direction by detecting the radiation irradiated from the radiation source head using the detector head while moving the radiation source head and the detector head together in a reciprocating manner in the width direction of the inspection target. In contrast, the "whole surface inspection type inspection apparatus" measures the distribution of the thickness of the inspection target in the width direction by detecting the linear radiation irradiated from the radiation source head using the line type detector of the detector head without moving the radiation source head and the detector head. Furthermore, Japanese Examined Utility Model Application, Second Publication No. H7-52573 and Japanese Unexamined Utility Model Application, First Publication No. S62-193505 respectively disclose the "scanning type inspection apparatus" and the "whole surface inspection type inspection apparatus" of the related art.

Incidentally, in the thickness inspecting apparatus, the inspection precision may be degraded due to reasons such as degradation in the radiation source head with the passage of time, a variation in the sensitivity of the detector, and a variation in the environment (periodic variations in the temperature and the humidity according to the weather, the time of day, or the like). For this reason, in any thickness inspecting apparatus between the "scanning type inspection apparatus" and the "whole surface inspection type inspection apparatus," there is a need to perform a correction in a state in which the inspection target is first removed and the radiation from the radiation source head is directly irradiated to the detector head.

The entire length of a production line used to conduct continuous production is as long as several tens to a hundred and several tens of meters, and the inspection target (product) may not be easily removed during the production. For this reason, for example, the best timing for the correction is considered to be a timing at which the inspection target is stopped so as to change the type of product or to pause the production. However, recently, production has often been conducted so that the inspection target is not stopped even for a short period of time by allowing a current product and a next product to be selected to be continuous to each other using a dummy sheet even when the type of product is changed, in order to improve the yield rate. Under the environment in which such production is conducted, the inspection target or the dummy sheet is normally present between the radiation source head and the detector head, which makes it difficult to perform a precise correction.

Here, in any thickness inspecting apparatus between the "scanning type inspection apparatus" and the "whole surface inspection type inspection apparatus," if an evacuation position is provided so as to allow the radiation source head and the detector head to face each other without interposing the inspection target or the dummy sheet therebetween, the precise correction may be performed even in a state in which the inspection target is not stopped. In the "scanning type inspection apparatus," the radiation source head and the detector head are small in size and do not need a large evacuation position. Accordingly, countermeasures of performing the correction by forming the evacuation position are realistic. However, since the "whole surface inspection type inspection apparatus" includes the detector head with a length approximately equal to the width of the inspection target, there is a need to form an evacuation position with a length approximately equal to the width of the inspection target. However, in a real production site, various units are often arranged with the narrowest gap therebetween so as to reduce the footprint. For this reason, it is not realistic to ensure the evacuation position with a length approximately equal to the width of the inspection target.

SUMMARY

The present invention provides a radiation inspection apparatus capable of performing a highly precise correction even in a state in which an inspection target or the like is disposed between a radiation source and a line type detector.

A radiation inspection apparatus may include: a radiation source that irradiates linear radiation, which is parallel to an inspection direction set on an inspection target, to the inspection target; a line type detector that detects the radiation transmitted through the inspection target; a correction detector that is disposed in at least one of a position between the radiation source and the inspection target and a position between the inspection target and the line type detector, the correction detector moving along the inspection direction to detect the radiation, which has been irradiated from the radiation source, at each of a plurality of inspection positions along the inspection direction; and a correction device that corrects the detection result of the line type detector by using the detection result of the correction detector.

The correction detector may be disposed between the radiation source and the inspection target. The correction device may include a dividing unit that divides the detection result of the line type detector by the detection result of the correction detector at each inspection position in the inspection direction.

The correction detector may be disposed between the inspection target and the line type detector. The correction device may include: a first calculation unit that obtains a thickness of the inspection target at each inspection position in the inspection direction based on the detection result of the line type detector; a second calculation unit that obtains a thickness of the inspection target at each inspection position in the inspection direction based on the detection result of the correction detector; a correction value calculating unit that obtains a correction value, which represents a difference between the thicknesses of the inspection target obtained by the first and second calculation units, at each inspection position in the inspection direction; and a correction unit that corrects the thickness of the inspection target, which has been obtained by the first calculation unit, by using the correction value, which has been obtained by the correction value calculating unit, at each inspection position in the inspection direction.

The correction value calculating unit may allow the thicknesses of the inspection target at the origin position obtained by the first and second calculation units to have the same value by using a difference between the thickness of the inspection target at a predetermined origin position in the inspection direction obtained by the first calculation unit and the thickness of the inspection target at the origin position obtained by the second calculation unit.

The correction detector may be disposed between the radiation source and the inspection target in addition to the position between the inspection target and the line type detector. The correction device may include a dividing unit that divides the detection result of the line type detector, which is used in the first calculation unit, by the detection result of the first correction detector, which is disposed between the radiation source and the inspection target, at each inspection position in the inspection direction, the dividing unit dividing the detection result of the second correction detector, which is disposed between the inspection target and the line type detector and is used in the second calculation unit, by the detection result of the first correction detector.

The dividing unit may normalize the detection result of the line type detector by using a ratio between the detection results of the line type detector and the correction detector at the predetermined origin position in the inspection direction.

The inspection direction may be set so as to intersect a direction in which the inspection target is transported.

A radiation inspection apparatus may include: a radiation source that is connected to a casing, the radiation source irradiating linear radiation, which is parallel to an inspection direction set on an inspection target, to the inspection target; a line type detector that is accommodated inside the casing, the line type detector including a plurality of detection elements arranged at constant intervals along the inspection direction, each of the detection elements detecting the radiation transmitted through the inspection target; a correction detector that is disposed in at least one of a position between the radiation source and the inspection target and a position between the inspection target and the line type detector, the correction detector moving along the inspection direction to detect the radiation, which has been irradiated from the radiation source, at each of a plurality of inspection positions along the inspection direction; and a correction device that corrects the detection result of the line type detector by using the detection result of the correction detector.

Part of the plurality of detection elements may be disposed at a position at which the radiation, which is irradiated from the radiation source and is not transmitted through the inspection target, is received.

The correction detector may be disposed between the radiation source and the inspection target. The correction device may include a dividing unit that divides the detection result of the line type detector by the detection result of the correction detector at each inspection position in the inspection direction.

The correction detector may be disposed between the inspection target and the line type detector. The correction device may include: a first calculation unit that obtains a thickness of the inspection target at each inspection position in the inspection direction based on the detection result of the line type detector; a second calculation unit that obtains a thickness of the inspection target at each inspection position in the inspection direction based on the detection result of the correction detector; a correction value calculating unit that obtains a correction value, which represents a difference between the thicknesses of the inspection target obtained by the first and second calculation units, at each inspection position in the inspection direction; and a correction unit that corrects the thickness of the inspection target, which has been obtained by the first calculation unit, by using the correction value, which has been obtained by the correction value calculating unit, at each inspection position in the inspection direction.

The correction value calculating unit may allow the thicknesses of the inspection target at the origin position obtained by the first and second calculation units to have the same value by using a difference between the thickness of the inspection target at a predetermined origin position in the inspection direction obtained by the first calculation unit and the thickness of the inspection target at the origin position obtained by the second calculation unit.

The correction detector may be disposed between the radiation source and the inspection target in addition to the position between the inspection target and the line type detector. The correction device may include a dividing unit that divides the detection result of the line type detector, which is used in the first calculation unit, by the detection result of the first correction detector, which is disposed between the radiation source and the inspection target, at each inspection position in the inspection direction, the dividing unit dividing the detection result of the second correction detector, which is disposed between the inspection target and the line type detector and is used in the second calculation unit, by the detection result of the first correction detector.

The dividing unit may normalize the detection result of the line type detector by using a ratio between the detection results of the line type detector and the correction detector at the predetermined origin position in the inspection direction.

The inspection direction may be set so as to intersect a direction in which the inspection target is transported.

A radiation inspection method may include: a first step of irradiating linear radiation, which is parallel to an inspection direction set on an inspection target, to the inspection target; a second step of detecting the radiation transmitted through the inspection target; a third step of detecting the irradiated radiation at each of a plurality of inspection positions along the inspection direction; and a fourth step of correcting the detection result of the second step by using the detection result of the third step.

The radiation inspection method may further include: a fifth step of dividing the detection result of the second step by the detection result of the third step at each of the plurality of inspection positions in the inspection direction.

The radiation inspection method may further include: a sixth step of obtaining a thickness of the inspection target at each inspection position in the inspection direction based on the detection result of the second step; a seventh step of obtaining a thickness of the inspection target at each inspection position in the inspection direction based on the detection result of the third step; an eighth step of obtaining a correction value, which represents a difference between the thicknesses of the inspection target obtained in the sixth step and the seventh step, at each inspection position in the inspection direction; and a ninth step of correcting the thickness of the inspection target, which has been obtained in the sixth step, by using the correction value, which has been obtained in the eighth step, at each inspection position in the inspection direction.

In the eighth step, the thicknesses of the inspection target at the origin position obtained in the sixth step and the seventh step may be made to be the same as each other by using a difference between the thickness of the inspection target at a predetermined origin position in the inspection direction obtained in the sixth step and the thickness of the inspection target at the origin position obtained in the seventh step.

In the fifth step, the detection result of the second step may be normalized by using a ratio between the detection results of the second step and the third step at the predetermined origin position in the inspection direction.

According to the present invention, a line type detector detects linear radiation which is irradiated from a radiation source to an inspection target and is transmitted through the inspection target, a correction detector which is movable along an inspection direction detects at least one of the linear radiation irradiated to the inspection target and the linear radiation transmitted through the inspection target, and the detection result of the line type detector is corrected by the detection result of the correction detector, thereby performing highly precise correction even in a state in which the inspection target or the like is disposed between the radiation source and the line type detector.

BRIEF DESCRIPTION OF THE DRAWINGS

The above features and advantages of the present invention will be more apparent from the following description of certain preferred embodiments taken in conjunction with the accompanying drawings, in which:

FIGS. 1A and 1B are diagrams illustrating a thickness inspecting apparatus as a radiation inspection apparatus in accordance with a first preferred embodiment of the present invention;

FIGS. 5A and 5B are diagrams illustrating a thickness inspecting apparatus as a radiation inspection apparatus in accordance with a second preferred embodiment of the present invention;

FIG. 10 is a flowchart illustrating an operation in accordance with the third preferred embodiment of the present invention.

DETAILED DESCRIPTION OF THE PREFERRED EMBODIMENTS

Figure 2:
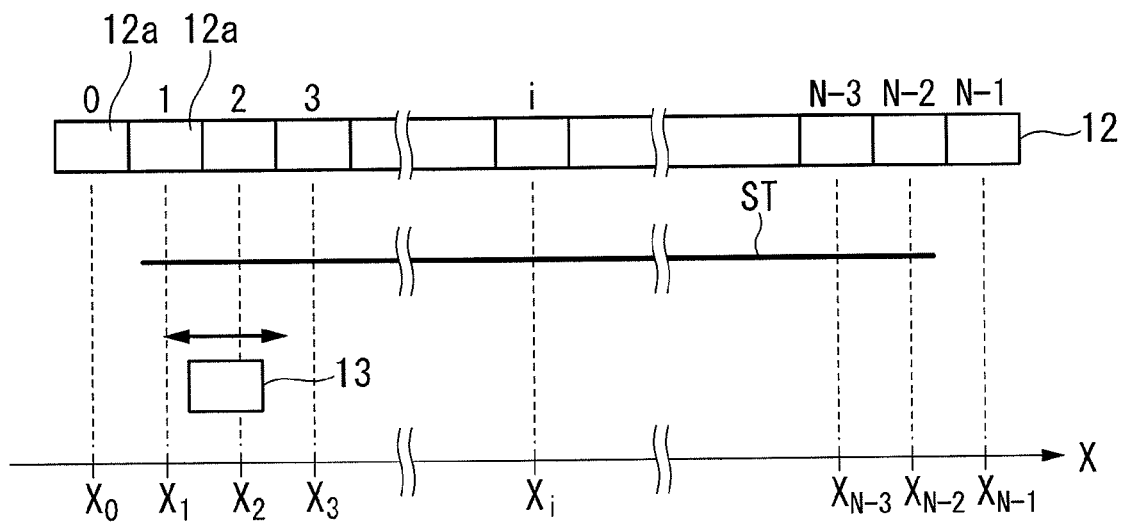
FIG. 2 is a diagram illustrating an inspection position in the X direction in accordance with the first preferred embodiment of the present invention.

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

Furthermore, hereinafter, a thickness inspecting apparatus which detects the thickness of a sheet online using radiation (for example, electromagnetic waves with a wavelength of 10 micron or more, such as X-rays, β-rays, γ-rays, ultraviolet rays, visible rays, infrared rays, and radio waves) will be described as an example. However, the present invention may be applied to a thickness inspecting apparatus which inspects the thickness or the amount of coating of a film online other than the thickness inspecting apparatus which inspects the thickness of the sheet.

First Preferred Embodiment

FIGS. 1A and 1B are diagrams illustrating a thickness inspecting apparatus as a radiation inspection apparatus in accordance with a first preferred embodiment of the present invention. FIG. 1A is a front perspective view, and FIG. 1B is a side perspective view. As shown in FIGS. 1A and 1B, a thickness inspecting apparatus 1 of this preferred embodiment includes a casing 10, a radiation source 11, a line type detector 12, and a correction detector 13. For example, the thickness inspecting apparatus is attached to a sheet producing line which is installed in a sheet producing factory and inspects a thickness of a sheet ST (an inspection target), which is produced by a sheet producing apparatus, using radiation.

Furthermore, in the following description, the positional relationships of respective members will be described referring to the XYZ orthogonal coordinate system which is set in the drawings, if necessary. However, for convenience of description, it is assumed that the origin of the XYZ orthogonal coordinate system shown in each of the drawings is not fixed and the position is appropriately changed for each of the drawings. In the XYZ orthogonal coordinate system shown in FIGS. 1A and 1B, the X axis is set as a direction along the width direction of the sheet ST (an inspection direction), the Y axis is set as a direction along a transportation direction of the sheet ST, and the Z axis is set as a direction along the vertical direction.

The casing 10 is a member of which the outer diameter shape is substantially formed in a rectangular parallelepiped shape with a hollow inside, and the casing 10 accommodates a radiation source 11, a line type detector 12, and a correction detector 13 therein. The vicinity of the upper end portion of the casing 10 (the vicinity of the end portion in the +Z direction) is provided with a notched portion 10a which extends from the end portion in the −X direction to the vicinity of the end portion in the +X direction and into which the sheet ST is inserted. Since the notched portion 10a is formed in the casing 10, it is possible to install or remove the thickness inspecting apparatus 1 without removing the sheet ST from the sheet producing line.

The radiation source 11 is fixed to the vicinity of the lower end portion inside the casing 10, and irradiates, for example, radiation such as X-rays, β-rays, and γ-rays toward the sheet ST. Specifically, the radiation source 11 is disposed below the sheet ST (one side: the −Z direction) in a state in which the sheet ST is inserted into the notched portion 10a of the casing 10, and irradiates linear radiation which extends in the X direction as the width direction of the sheet ST to the bottom surface of the sheet ST.

The line type detector 12 is fixed to the vicinity of the upper end portion inside the casing 10, and detects the linear radiation which is transmitted through the sheet ST. Specifically, the line type detector 12 includes a plurality of detection elements 12a (for example, a semiconductor detection element such as a silicon photodiode) which are arranged at constant intervals along the X direction, and is disposed so as to be fixed to a position which is above the notched portion 10a formed in the casing 10 (the other side: the +Z direction) and to which the radiation transmitted through the sheet ST is irradiated. With regard to the line type detector 12, it is desirable that a part of the detection element 12a be disposed at a position where the radiation which is irradiated from the radiation source 11 and is not transmitted through the sheet ST is received.

Hereinafter, in order to facilitate understanding, it is assumed that the line type detector 12 includes N (N is an integer greater than or equal to 2) detection elements 12a and the respective detection elements 12a are distinguished from each other by the numerals "0" to "N−1" as shown in FIG. 2. FIG. 2 is a diagram illustrating an inspection position in the X direction in accordance with the first preferred embodiment of the present invention. Here, the thickness of the sheet ST in the X direction is inspected based on the detection result of each of the detection elements 12a which are provided in the line type detector 12. For this reason, the positions $X_0$ to $X_{N-1}$ in the X direction in which the detection elements 12a denoted by the numerals "0" to "N−1" shown in FIG. 2 are arranged may be defined as the inspection positions in the X direction. Hereinafter, the inspection position $X_0$ in the X direction is defined as the "origin position." Furthermore, the inspection position $X_{N-1}$ may be defined as the "origin position."

The correction detector 13 includes a semiconductor detection element such as a silicon photodiode, is disposed between the radiation source 11 and the sheet ST, and detects the radiation from the radiation source 11 while moving along the movement direction D1 (the X direction: the inspection direction) shown in FIG. 1A. Specifically, the correction detector 13 is disposed near the downside of the notched portion 10a inside the casing 10 as shown in FIGS. 1A and 1B, and the movement path thereof is set so that the correction detector 13 crosses the linear radiation irradiated from the radiation source 11 in the X direction. Furthermore, although it is not shown in FIGS. 1A and 1B, the casing 10 accommodates a mechanism which moves the correction detector 13 in a reciprocating manner along the X direction. The detection result of the correction detector 13 is used to correct the detection result of the line type detector 12.

Here, when the radiation from the radiation source 11 is detected by moving the correction detector 13 along the movement direction D1, the continuous distribution of the radiation in the X direction may be detected. However, in this preferred embodiment, for simplicity of description, the inspection in the correction detector 13 is also performed at the inspection positions $X_0$ to $X_{N-1}$ shown in FIG. 2. That is, it is assumed that the discrete detection results are obtained at the inspection positions $X_0$ to $X_{N-1}$ when the radiation is detected by moving the correction detector 13 along the movement direction D1.

Figure 3:
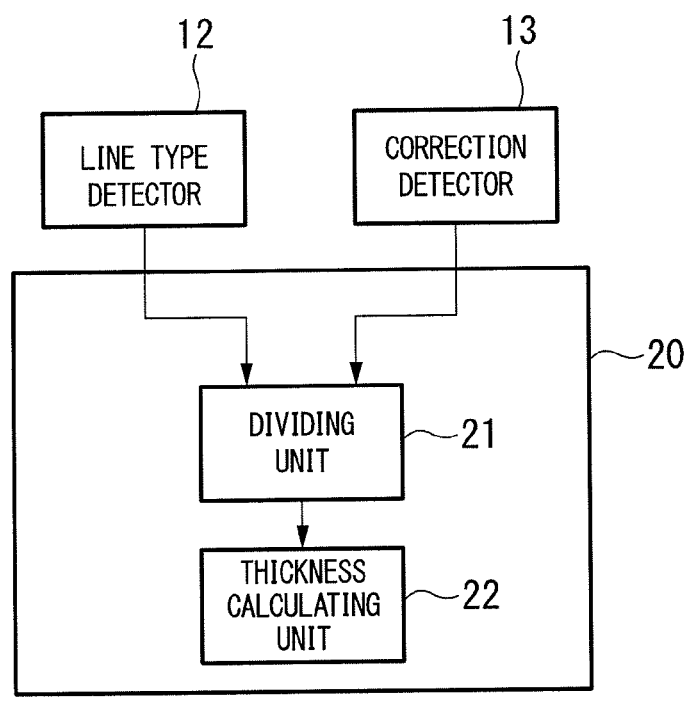
FIG. 3 is a block diagram illustrating a main part of a processing device in accordance with the first preferred embodiment of the present invention.

Next, a signal processing device which is included in the thickness inspecting apparatus 1 will be described. FIG. 3 is a block diagram illustrating a main part of the signal processing device in accordance with the first preferred embodiment of the present invention. As shown in FIG. 3, a signal processing device 20 (a correction device) includes a dividing unit 21 and a thickness calculating unit 22, and obtains the thickness of the sheet ST by performing a signal process on the detection signals of the line type detector 12 and the correction detector 13. Specifically, the detection result of the line type detector 12 is corrected using the detection result of the detection signal of the correction detector 13, and the thickness of the sheet ST is obtained using the corrected detection result of the line type detector 12.

The dividing unit 21 corrects the detection result of the line type detector 12 using the detection result of the detection signal of the correction detector 13. Specifically, a ratio between the detection result of the line type detector 12 and the detection result of the correction detector 13 at the origin position is obtained, and a value obtained by dividing the detection result of the correction detector 13 from the detection result of the line type detector 12 at each of the inspection positions $X_0$ to $X_{N-1}$ is multiplied by the ratio, thereby correcting the detection result of the line type detector 12. Furthermore, the detection result of the line type detector 12 which is corrected in the above-described process is normalized so that the value at the origin position becomes "1."

Here, the detection result of the line type detector 12 is affected by the following factors (A) to (C).
(A) intensity distribution of radiation in X direction
(B) thickness distribution of sheet ST in X direction
(C) instrumental error of detection element 12a In contrast, the detection result of the correction detector 13 is affected by the following factors (A) and (D).
(A) intensity distribution of radiation in X direction
(D) positional error in movement along movement direction D1

The dividing unit 21 excludes the influence caused by factor (A) by dividing the detection result of the correction detector 13 from the detection result of the line type detector 12 at each inspection position. Furthermore, the influence caused by factor (D) is neglected since it is smaller than the influence caused by factors (A) to (C), but may be corrected if necessary. For example, a sensor which detects the positional error of the correction detector 13 is provided, and the detection result of the correction detector 13 is corrected based on the detection result of the sensor.

Specifically, under the assumption that the detection result of the line type detector 12 is denoted by A(i) and the detection result of the correction detector 13 is denoted by B(i), the dividing unit 21 may exclude the influence caused by factor (A) by calculating the following equation (1). Furthermore, the variable i is an integer which satisfies the equation of $0 \le i \le N$.

$$R \cdot A(i)/B(i) \qquad (1)$$

Here, the variable R in equation (1) denotes the ratio (R=A(0)/B(0)) between the detection result of the line type detector 12 and the detection result of the correction detector 13 at the origin position.

The thickness calculating unit 22 detects the thickness of the sheet ST (the thickness of the sheet ST at each of the inspection positions $X_0$ to $X_{N-1}$ shown in FIG. 2) in the X direction by performing a thickness calculation on the detection result of the line type detector 12 corrected by the dividing unit 21. Here, since the influence caused by factor (A) is excluded from the detection result of the line type detector 12 corrected by the dividing unit 21, the influence caused by factor (A) is also excluded from the thickness of the sheet ST detected by the thickness calculating unit 22.

Next, the operation of the thickness inspecting apparatus 1 with the above-described configuration will be described. The operation of the thickness inspecting apparatus 1 is broadly classified into an operation of detecting the thickness distribution of the transported sheet ST in the X direction and an operation of correcting the detection result of the line type detector 12, but hereinafter, the latter operation will be mainly described. Furthermore, the latter operation is performed in a state in which the transportation of the sheet ST is stopped and the sheet ST (or a dummy sheet which connects the sheet ST) is inserted into the notched portion 10a of the casing 10.

Figure 4:
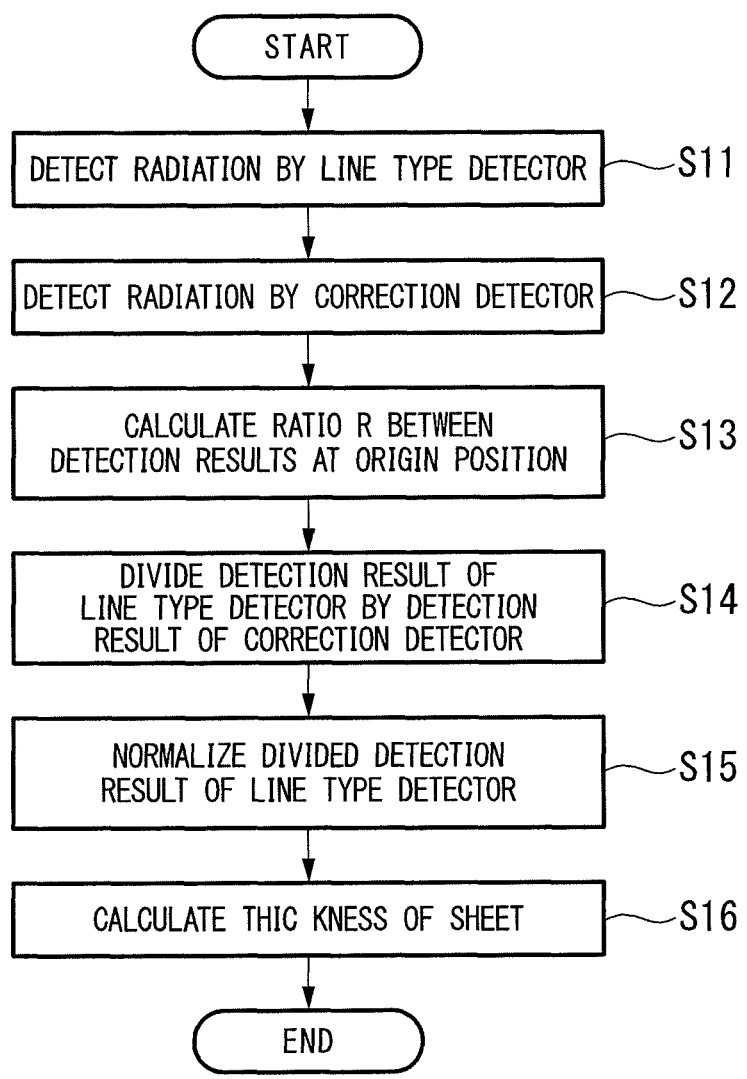
FIG. 4 is an example of a flowchart illustrating an operation in accordance with the first preferred embodiment of the present invention.

FIG. 4 is an example of a flowchart illustrating an operation in accordance with the first preferred embodiment of the present invention. When the operation of the thickness inspecting apparatus 1 is started, first, the linear radiation which extends in the X direction is irradiated from the radiation source 11 to the bottom surface of the sheet ST, and the linear radiation which is transmitted through the sheet ST is detected by the line type detector 12 (step S11). When the detection of the radiation using the line type detector 12 ends, the movement of the correction detector 13 in the movement direction D1 (for example, the +X direction) is started by a mechanism (not shown) which is accommodated in the casing 10, and the linear radiation which is irradiated from the radiation source 11 is detected by the correction detector 13 (step S12). Furthermore, the detection results using the line type detector 12 and the correction detector 13 are input to the signal processing device 20.

When both the detection result of the line type detector 12 and the detection result of the correction detector 13 are input to the signal processing device 20, first, the dividing unit 21 calculates the ratio R between the detection results at the origin position (step S13). Specifically, the detection result of the line type detector 12 A(0) at the origin position is divided by the detection result of the correction detector 13 B(0) at the origin position, thereby calculating the ratio R.

Subsequently, the dividing unit 21 performs a process of dividing the detection result of the line type detector 12 by the detection result of the correction detector 13 at each of the inspection positions $X_0$ to $X_{N-1}$ (step S14). Specifically, a process is performed in which the detection result of the line type detector 12 A(i) is divided by the detection result of the correction detector 13 B(i). Next, the dividing unit 21 performs a process of normalizing the divided detection result of the line type detector 12 (step S15).

Specifically, a process is performed in which the ratio R calculated in step S13 is multiplied by the detection result of the line type detector 12 divided in step S14.

With the above-described process, the detection result of the line type detector 12 is corrected so that the influence caused by the factor of the intensity distribution of the radiation in the X direction shown in (A) is excluded and is normalized so that the value at the origin position becomes "1." When the above-described process ends, the corrected detection result of the line type detector 12 is output to the thickness calculating unit 22, so that the thickness is calculated (step S16). Accordingly, the thickness of the sheet ST (the thickness of the sheet ST at each of the inspection positions $X_0$ to $X_{N-1}$ shown in FIG. 2) in the X direction is detected.

Furthermore, in the above description, in order to facilitate understanding, the operation sequence is distributed to step S11 and step S12, but may be appropriately changed or combined. Further, the process which is performed by the divider 21 is described as the separate processes of step S13 to step S15, but the processes of step S14 and step S15 may be performed together by calculating equation (1). By performing such a process, a time necessary for the calculation or the process may be shortened.

As described above, in this preferred embodiment, the correction detector 13 which is movable along the movement direction D1 is provided between the radiation source 11 and the sheet ST, and the detection result of the line type detector 12 is divided by the detection result of the correction detector 13 so as to be normalized. For this reason, even in a state in which the sheet ST or the dummy sheet is disposed between the radiation source 11 and the line type detector 12, the detection result of the line type detector 12 may be corrected so that the influence caused by the factor of the intensity distribution of the radiation in the X direction is excluded.

Second Preferred Embodiment

FIGS. 5A and 5B are diagrams illustrating a thickness inspecting apparatus as a radiation inspection apparatus in accordance with a second preferred embodiment of the present invention. FIG. 5A is a front perspective view, and FIG. 5B is a side perspective view. As shown in FIGS. 5A and 5B, a thickness inspecting apparatus 2 of this preferred embodiment includes a correction detector 14 instead of the correction detector 13 which is included in the thickness inspecting apparatus 1 shown in FIGS. 1A and 1B.

The correction detector 14 includes a semiconductor detection element such as a silicon photodiode as in the correction detector 13. However, unlike the correction detector 13, the correction detector 14 is disposed between the sheet ST and the line type sensor 12, and detects the radiation from the radiation source 11 while moving along the movement direction D1 (the X direction) shown in FIG. 5A. Specifically, the correction detector 14 is disposed between the notched portion 10a and the line type sensor 12 inside the casing 10 as shown in FIGS. 5A and 5B, and the movement path thereof is set so that the correction detector 14 crosses the linear radiation irradiated from the radiation source 11 in the X direction.

Furthermore, although it is not shown in FIGS. 5A and 5B, the casing 10 accommodates a mechanism which moves the correction detector 14 in a reciprocating manner along the X direction. Further, in this preferred embodiment as well, for simplicity of description, the discrete detection results at the inspection positions $X_0$ to $X_{N-1}$ are obtained when the radiation is detected by moving the correction detector 14 along the movement direction D1 as when the radiation is detected by moving the correction detector 13 along the movement direction D1.

Figure 6:
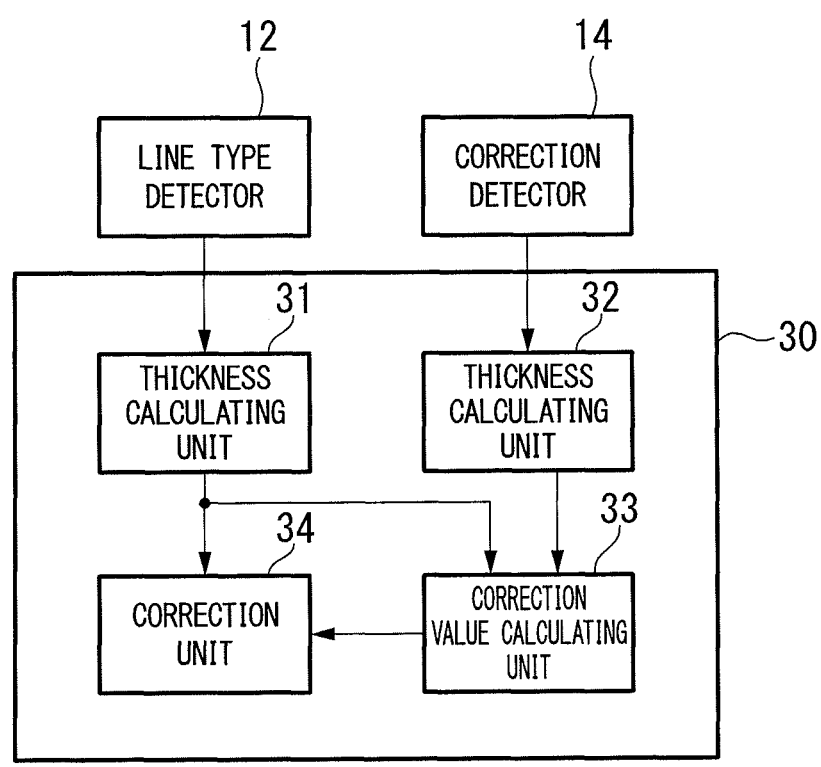
FIG. 6 is a block diagram illustrating a configuration of a main part of the signal processing device in accordance with the second preferred embodiment of the present invention.

FIG. 6 is a block diagram illustrating a configuration of a main part of the signal processing device in accordance with the second preferred embodiment of the present invention. As shown in FIG. 6, the signal processing device 30 (the correction device) includes a thickness calculating unit 31 (a first calculation unit), a thickness calculating unit 32 (a second calculation unit), a correction value calculating unit 33, and a correction unit 34, and obtains the thickness of the sheet ST by performing a signal process on the detection signals of the line type detector 12 and the correction detector 14.

Specifically, each thickness of the sheet ST is calculated using the detection signals of the line type detector 12 and the correction detector 14, a correction value representing a difference in the obtained thickness is obtained, and the thickness obtained using the detection signal of the line type detector 12 is corrected by the correction value. The thickness calculating unit 31 obtains the thickness of the sheet ST (the thickness of the sheet ST at each of the inspection positions $X_0$ to $X_{N-1}$ shown in FIG. 2) in the X direction by performing a thickness calculation on the detection result of the line type detector 12. The thickness calculating unit 32 obtains the thickness of the sheet ST (the thickness of the sheet ST at each of the inspection positions $X_0$ to $X_{N-1}$ shown in FIG. 2) in the X direction by performing a thickness calculation on the detection result of the correction detector 14.

The correction value calculating unit 33 obtains a correction value which represents a difference between the thickness obtained by the thickness calculating unit 31 and the thickness obtained by the thickness calculating unit 32 at each of the inspection positions $X_0$ to $X_{N-1}$. Specifically, first, a ratio between the thickness at the origin position obtained by the thickness calculating unit 31 and the thickness at the origin position obtained by the thickness calculating unit 32 is obtained. Then, the thickness obtained by the thickness calculating unit 32 is subtracted from a value which is obtained by multiplying the thickness obtained by the thickness calculating unit 31 at each of the inspection positions $X_0$ to $X_{N-1}$ by the ratio, thereby calculating the correction value.

The correction unit 34 corrects the thickness obtained by the thickness calculating unit 31 at each of the inspection positions $X_0$ to $X_{N-1}$ by the correction value obtained by the correction value calculating unit 33. Specifically, the correction value at each of the inspection positions $X_0$ to $X_{N-1}$ calculated by the correction value calculating unit 33 is subtracted from the thickness at each of the inspection positions $X_0$ to $X_{N-1}$ obtained by the thickness calculating unit 31, thereby correcting the thickness obtained by the thickness calculating unit 31.

Here, the detection result of the line type detector 12 is affected by the following factors (A) to (C) as described above.

(A) intensity distribution of radiation in X direction
(B) thickness distribution of sheet ST in X direction
(C) instrumental error of detection element 12a In contrast, the detection result of the correction detector 14 is affected by the following factors (A), (B), and (D).

(A) intensity distribution of radiation in X direction
(B) thickness distribution of sheet ST in X direction
(D) positional error in movement along movement direction D1

The signal processing device 30 first obtains the thickness of the sheet ST using the detection results of the line type detector 12 and the correction detector 14, obtains the correction value representing a difference in the thickness, and then corrects the thickness of the sheet ST obtained using the detection result of the line type detector 12 by the correction value, thereby excluding factors (A) and (B). Furthermore, the influence caused by factor (D) negligibly decreases as in the first preferred embodiment. Specifically, under the assumption that the thickness obtained from the detection result of the line type detector 12 is denoted by $T1(i)$ and the thickness obtained from the detection result of the correction detector 14 is denoted by $T2(i)$, the correction value calculating unit 33 calculates the correction value $A(i)$ by calculating the following equation (2).

$$A(i) = Q \cdot T1(i) - T2(i) \qquad (2)$$

Here, the variable Q in equation (2) denotes the ratio ($Q = T1(0)/T2(0)$) between the thickness obtained from the detection result of the line type detector 12 and the thickness obtained from the detection result of the correction detector 14 at the origin position.

The correction unit 34 corrects the thickness $T1(i)$ obtained from the detection result of the line type detector 12 by calculating the following equation (3).

$$T1(i) - A(i) \qquad (3)$$

With regard to the thickness obtained by the calculation of equation (3), the influence caused by factors (A) and (B) is excluded.

Next, the operation of the thickness inspecting apparatus 2 with the above-described configuration will be described. Furthermore, in this preferred embodiment as well, an operation in which the detection result of the line type detector 12 is corrected in a state in which the transportation of the sheet ST is stopped and the sheet ST (or the dummy sheet which connects the sheet ST) is inserted into the notched portion 10a of the casing 10 will be mainly described.

Figure 7:
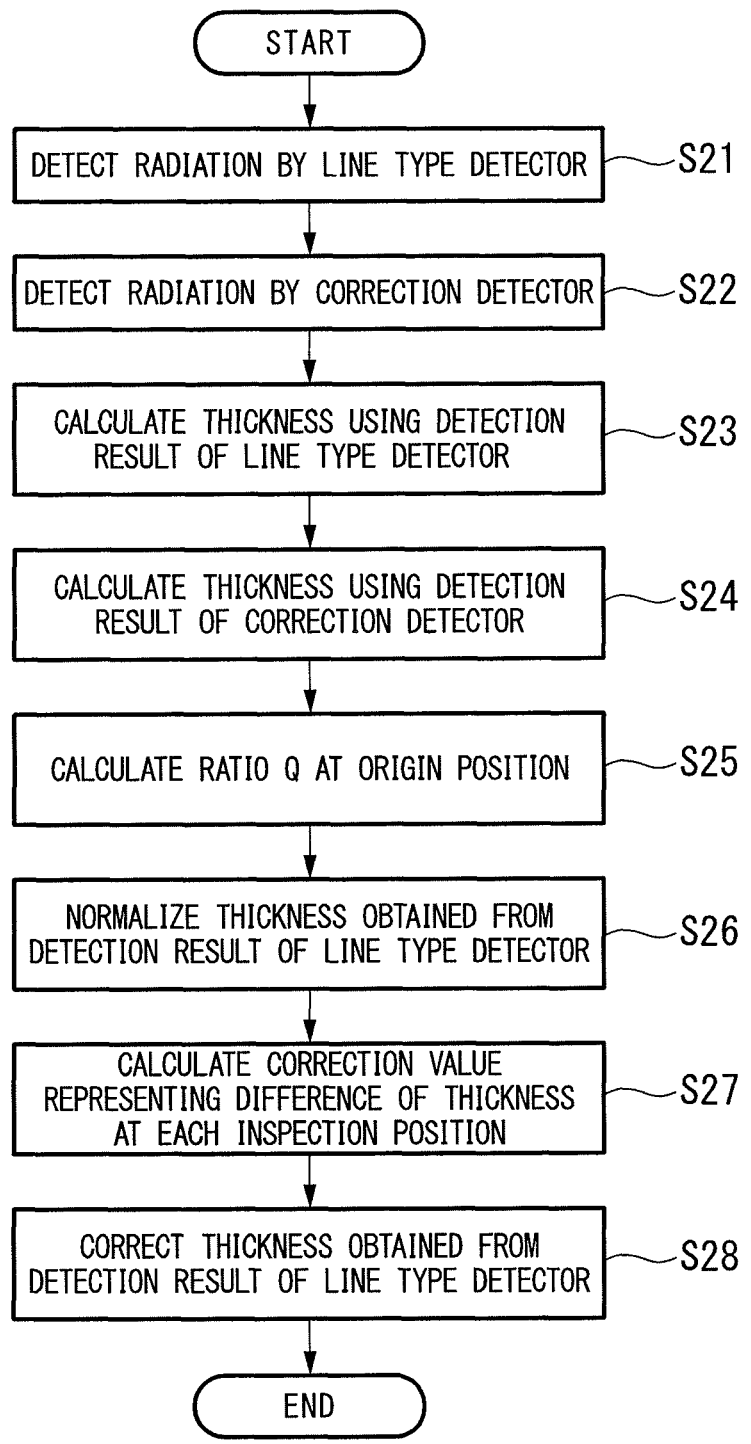
FIG. 7 is an example of a flowchart illustrating an operation in accordance with the second preferred embodiment of the present invention.

FIG. 7 is an example of a flowchart illustrating an operation in accordance with the second preferred embodiment of the present invention. When the operation of the thickness inspecting apparatus 1 is started, first, the linear radiation which extends in the X direction is irradiated from the radiation source 11 to the bottom surface of the sheet ST, and the linear radiation which is transmitted through the sheet ST is detected by the line type detector 12 (step S21). When the detection of the radiation using the line type detector 12 ends, the movement of the correction detector 14 in the movement direction D1 (for example, the +X direction) is started by a mechanism (not shown) which is accommodated in the casing 10, and the linear radiation which is irradiated from the radiation source 11 is detected by the correction detector 14 (step S22). Furthermore, the detection results using the line type detector 12 and the correction detector 14 are input to the signal processing device 30.

When the detection result of the line type detector 12 is input to the signal processing device 30, the thickness calculation is performed by the thickness calculating unit 31, so that the thickness of the sheet ST at each of the inspection positions $X_0$ to $X_{N-1}$ is obtained (step S23). In the same way, when the detection result of the correction detector 14 is input to the signal processing device 30, the thickness calculation is performed by the thickness calculating unit 32, so that the thickness of the sheet ST at each of the inspection positions $X_0$ to $X_{N-1}$ is obtained (step S24). The calculation result of the thickness calculating unit 31 is output to the correction value calculating unit 33 and the correction unit 34, and the calculation result of the thickness calculating unit 32 is output only to the correction value calculating unit 33. When the calculation results of the thickness calculating units 31 and 32 are input, the correction value calculating unit 33 calculates a ratio Q between the thicknesses at the origin position (step S25). Specifically, the thickness T1(0) at the origin position obtained by the thickness calculating unit 31 is divided by the thickness T2(0) at the origin position obtained by the thickness calculating unit 32, thereby calculating the ratio Q.

Subsequently, the correction value calculating unit 33 performs a process of normalizing the thickness T1(i) obtained by the thickness calculating unit 31 (step S26).

Specifically, a process is performed in which the ratio Q calculated in step S25 is multiplied by the thickness T1(i) obtained by the thickness calculating unit 31. Then, the correction value calculating unit 33 performs a process of calculating the correction value A(i) at each of the inspection positions $X_0$ to $X_{N-1}$ (step S27). Specifically, a process is performed in which the thickness T2(i) obtained by the thickness calculating unit 32 is subtracted from the thickness T1(i) normalized in step S26.

The correction value A(i) which is calculated by the correction value calculating unit 23 is output to the correction unit 34, and the correction unit 34 performs a process of correcting the thickness T1(i) obtained by the thickness calculating unit 31 by the correction value A(i) (step S28). Specifically, equation (3) is calculated. With regard to the thickness of the sheet ST which is obtained by the above-described process, the influence caused by the factor of the intensity distribution of the radiation in the X direction shown in (A) and the influence caused by the factor of the thickness distribution of the sheet ST in the X direction shown in (B) are excluded.

Furthermore, in the description above, in order to facilitate understanding, the process which is performed by the correction value calculating unit 33 is described as separate processes in step S25 to step S27, but the processes of step S26 and step S27 may be performed together by calculating equation (2). By performing such a process, a time necessary for the calculation or the process may be shortened. Further, the sequences of step S21, step S22 and step S23, and step S24 may be appropriately changed or combined.

As described above, in this preferred embodiment, the correction detector 14 which is movable along the movement direction D1 is provided between the sheet ST and the line type detector 12, and the thickness of the sheet obtained from the detection result of the line type detector 12 is corrected by the thickness of the sheet obtained from the detection result of the correction detector 14. For this reason, even in a state in which the sheet ST or the dummy sheet is disposed between the radiation source 11 and the line type detector 12, the thickness of the sheet ST may be obtained so that the influences caused by the factor of the intensity distribution of the radiation in the X direction and the factor of the thickness distribution of the sheet ST in the X direction are excluded.

Third Preferred Embodiment

Figure 8B:
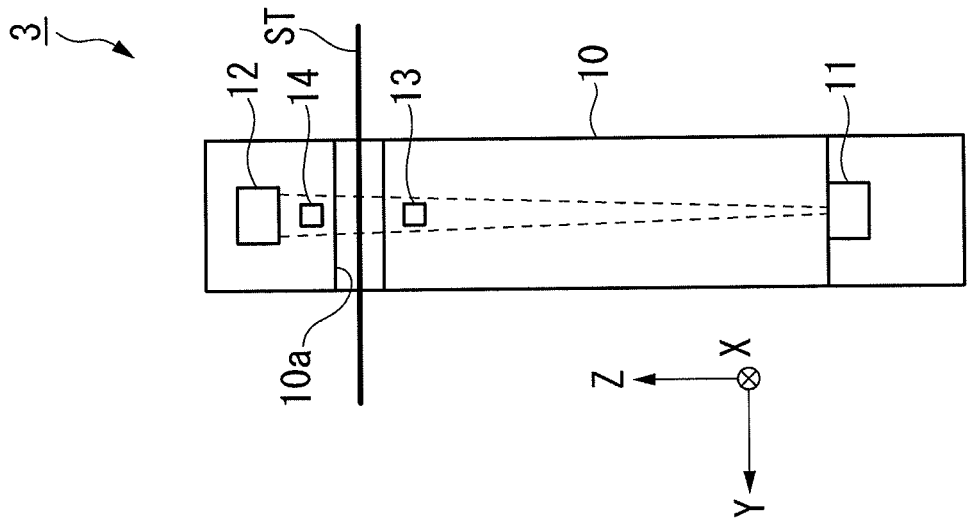
FIGS. 8A and 8B are diagrams illustrating a thickness inspecting apparatus as a radiation inspection apparatus in accordance with a third preferred embodiment of the present invention.
Figure 8A:
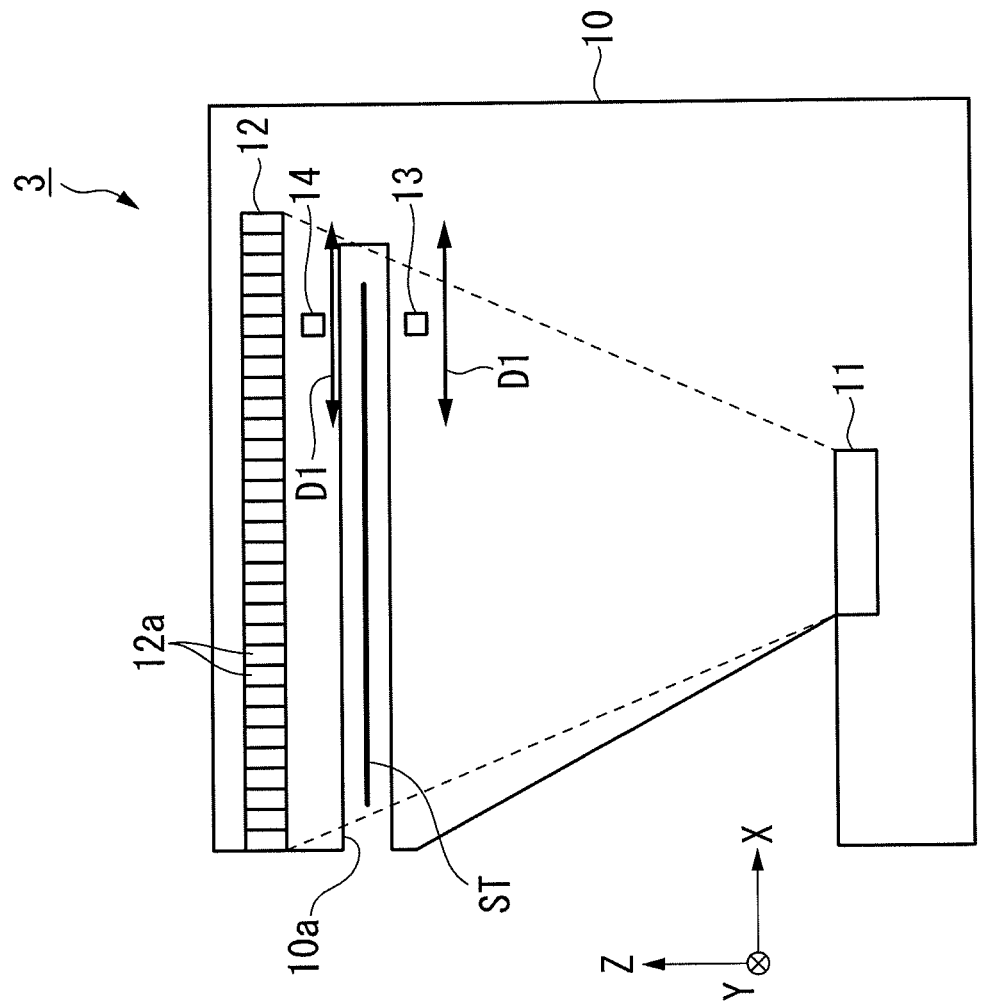

FIGS. 8A and 8B are diagrams illustrating a thickness inspecting apparatus as a radiation inspection apparatus in accordance with a third preferred embodiment of the present invention. FIG. 8A is a front perspective view, and FIG. 8B is a side perspective view. As shown in FIGS. 8A and 8B, a thickness inspecting apparatus 3 of this preferred embodiment includes both the correction detector 13 which is included in the thickness inspecting apparatus 1 shown in FIGS. 1A and 1B and the correction detector 14 which is included in the thickness inspecting apparatus 2 shown in FIGS. 5A and 5B.

Figure 9:
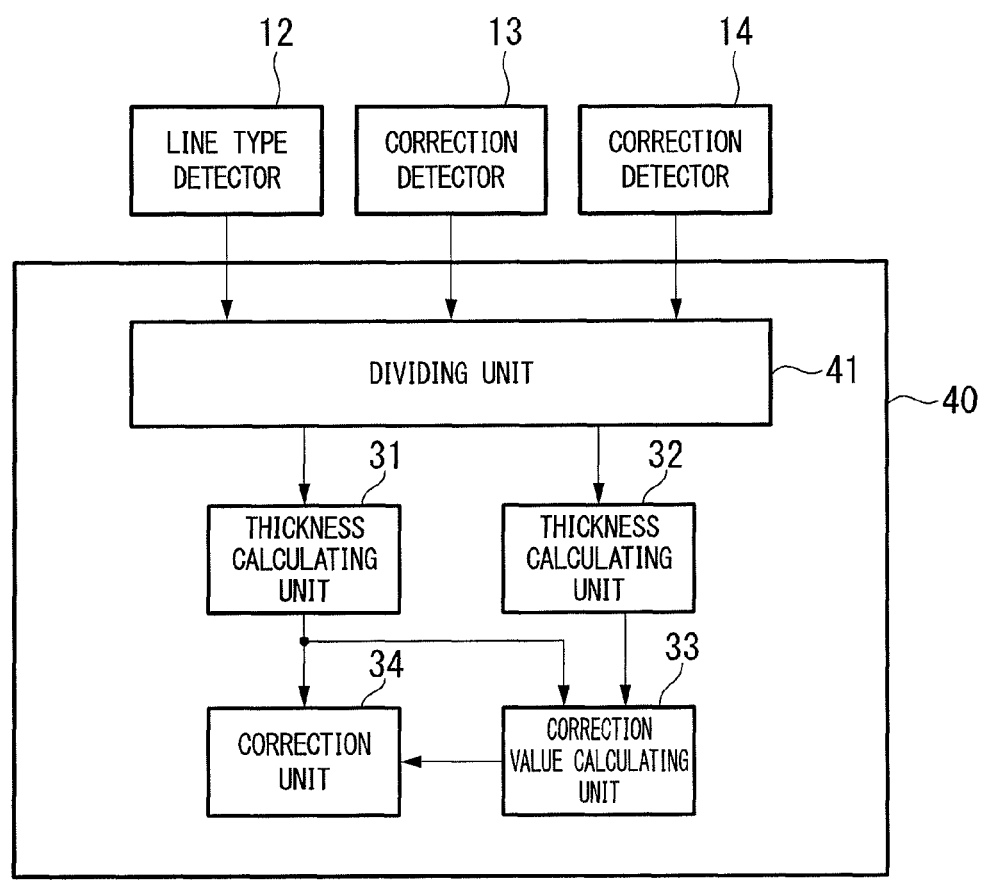
FIG. 9 is a block diagram illustrating a configuration of a main part of the signal processing device in accordance with the third preferred embodiment of the present invention.

FIG. 9 is a block diagram illustrating a configuration of a main part of the signal processing device in accordance with the third preferred embodiment of the present invention. As shown in FIG. 9, the signal processing device 40 (the correction device) further includes a dividing unit 41 in addition to the thickness calculating unit 31 to the correction unit 34 which are included in the signal processing device 30 shown in FIG. 6. The dividing unit 41 corrects the detection results of the line type detector 12 and the correction detector 14 using the detection result of the detection signal of the correction detector 13.

Specifically, a ratio between the detection result of the line type detector 12 and the detection result of the correction detector 13 at the origin position is obtained, and the ratio is multiplied by the value obtained by dividing the detection result of the line type detector 12 by the detection result of the correction detector 13 at each of the inspection positions $X_0$ to $X_{N-1}$, thereby correcting the detection result of the line type detector 12. In the same way, a ratio between the detection result of the correction detector 14 and the detection result of the correction detector 13 at the origin position is obtained, and the ratio is multiplied by the value obtained by dividing the detection result of the correction detector 14 by the detection result of the correction detector 13 at each of the inspection positions $X_0$ to $X_{N-1}$, thereby correcting the detection result of the correction detector 14. Furthermore, the detection results of the line type detector 12 and the correction detector 14 corrected by the above-described process are normalized so that the value at the origin position becomes "1."

The dividing unit 41 excludes the influence caused by the factor (A) from the detection result of the line type detector 12 by dividing the detection result of the correction detector 13 from the detection result of the line type detector 12 at each inspection position. In the same way, the dividing unit excludes the influence caused by the factor (A) from the detection result of the correction detector 14 by dividing the detection result of the correction detector 14 by the detection result of the correction detector 13 at each inspection position.

Specifically, under the assumption that the detection result of the line type detector 12 is denoted by A(i), the detection result of the correction detector 13 is denoted by B(i), and the detection result of the correction detector 14 is denoted by C(i), the dividing unit 41 excludes the influence caused by the factor (A) from the detection result of the line type detector 12 by calculating the following equation (4), and excludes the influence caused by the factor (A) from the detection result of the correction detector 14 by calculating the following equation (5).

$$R1 \cdot A((i)/B(i) \quad (4)$$

$$R2 \cdot C(i)/B(i) \quad (5)$$

Here, the variable R1 in equation (4) denotes the ratio (R=A(0)/B(0)) between the detection result of the line type detector 12 and the detection result of the correction detector 13 at the origin position. Further, the variable R2 in equation (5) denotes the ratio (R2=C(0)/B(0)) between the detection result of the correction detector 13 and the detection result of the correction detector 14 at the origin position.

Next, the operation of the thickness inspecting apparatus 3 with the above-described configuration will be described. Furthermore, in this preferred embodiment as well, an operation of correcting the detection result of the line type detector 12 in a state in which the transportation of the sheet ST is stopped and the sheet ST (or the dummy sheet which connects the sheet ST) is inserted into the notched portion 10a of the casing 10 will be mainly described.

FIG. 10 is a flowchart illustrating an operation in accordance with the third preferred embodiment of the present invention. When the operation of the thickness inspecting apparatus 1 is started, first, the linear radiation which extends in the X direction is irradiated from the radiation source 11 to the bottom surface of the sheet ST, and the linear radiation which is transmitted through the sheet ST is detected by the line type detector 12 (step S31). When the detection of the radiation using the line type detector 12 ends, the movement of the correction detectors 13 and 14 along the movement direction D1 (for example, the +X direction) is sequentially started, and the linear radiation irradiated from the radiation source 11 is sequentially detected by the correction detectors 13 and 14 (step S32). Furthermore, the detection results using the line type detector 12 and the correction detectors 13 and 14 are input to the signal processing device 40.

When the detection results of the line type detector 12 and the correction detectors 13 and 14 are input to the signal processing device 40, the dividing unit 41 calculates the ratio R1 between the detection results of the line type detector 12 and the correction detector 13 at the origin position (step S33). Specifically, the detection result of the line type detector 12 A(0) at the origin position is divided by the detection result of the correction detector 13 B(0) at the origin position, thereby calculating the ratio R1. Subsequently, the dividing unit 41 calculates the ratio R2 between the detection results of the correction detectors 13 and 14 at the origin position (step S34). Specifically, the detection result of the correction detector 14 C(0) at the origin position is divided by the detection result of the correction detector 13 B(0) at the origin position, thereby calculating the ratio R2.

Subsequently, the dividing unit 41 performs a process of dividing the detection result of the line type detector 12 by the detection result of the correction detector 13 at each of the inspection positions $X_0$ to $X_{N-1}$ (step S35). Specifically, a process is performed in which the detection result of the line type detector 12 A(i) is divided by the detection result of the correction detector 13 B(i). Then, the dividing unit 41 performs a process of normalizing the divided detection result of the line type detector 12 (step S36). Specifically, a process is performed in which the ratio R1 calculated in step S33 is multiplied by the detection result of the line type detector 12 divided in step S35. Further, the dividing unit 41 performs a process of dividing the detection result of the correction detector 14 by the detection result of the correction detector 13 at each of the inspection positions $X_0$ to $X_{N-1}$ (step S37). Specifically, a process is performed in which the detection result of the correction detector 14 C(i) is divided by the detection result of the correction detector 13 B(i). Then, the dividing unit 41 performs a process of normalizing the divided detection result of the correction detector 14 (step S38).

Specifically, a process is performed in which the ratio R2 calculated in step S34 is multiplied by the detection result of the correction detector 14 divided in step S37.

When the above-described process ends, the detection result of the line type detector 12 normalized in step S36 is output to the thickness calculating unit 31, and the detection result of the correction detector 14 normalized in step S38 is output to the thickness calculating unit 32. Then, the processes of step S23 to step S28 shown in FIG. 7 are sequentially performed.

Furthermore, in the description above, in order to facilitate understanding, the process performed by the dividing unit 41 is divided as separate processes of step S33 to step S38. However, the processes of step S35 and step S36 may be performed together by performing the calculation of equation (4), and the processes of step S37 and step S38 may be performed together by performing the calculation of equation (5). By performing such a process, the time necessary for the calculation or the process may be shortened.

As described above, in this preferred embodiment, the correction detector 13 which is movable along the movement direction D1 is provided between the radiation source 11 and the sheet ST, the correction detector 14 which is movable along the movement direction D1 is provided between the sheet ST and the line type detector 12, the detection results of the line type detector 12 and the correction detector 14 are corrected using the detection result of the correction detector 14, and then the processes of step S23 to step S28 of the second preferred embodiment are performed. For this reason, even in a state in which the sheet ST or the dummy sheet having a large thickness is disposed between the radiation source 11 and the line type detector 12, it is possible to highly precisely obtain the thickness of the sheet ST in which the influence caused by the factor of the intensity distribution of the radiation in the X direction and the influence caused by the factor of the thickness distribution of the sheet ST in the X direction are excluded.

The radiation inspection apparatuses in accordance with the preferred embodiments of the present invention have been described above, but the present invention is not limited to the above-described preferred embodiments and may be freely modified without departing from the scope of the present invention. For example, the radiation is detected by moving the correction detectors 13 and 14 in a reciprocating manner multiple times along the X direction, and the respective detection results are averaged, thereby improving the precision. Further, in the description above, an example in which the value at the origin position is normalized so as to become "1" has been described, but the normalized value may be multiplied by the appropriate integer in order to easily treat the detection result of the line type detector 12.

Further, in the above-described preferred embodiments, an example in which the correction detectors 13 and 14 include a semiconductor detection element such as a silicon photodiode has been described, but the correction detectors 13 and 14 may be provided with a scintillation detector, a counter tube, an ionization chamber, or the like. That is, the detector which is provided in the correction detectors 13 and 14 may be appropriately selected in accordance with the wavelength band or the characteristics of the radiation irradiated from the radiation source 11.

Further, a process of correcting the detection result in accordance with the distances of the line type detector 12 and the correction detectors 13 and 14 may be added. Furthermore, a process of correcting the detection result in accordance with an angle formed by the radiation source 11 that changes in accordance with the arrangement positions of the detection elements 12a of the line type detector 12 in the X direction and the positions of the correction detectors 13 and 14 in the X direction may be added.

Further, in the above-described preferred embodiments, in order to facilitate understanding, a configuration including only the correction detector 13 (the first preferred embodiment), a configuration including only the correction detector 14 (the second preferred embodiment), and a configuration including both of the correction detectors 13 and 14 (the third preferred embodiment) have been described. However, it is desirable that the processes shown in FIGS. 4, 7, and 10 be changed according to the command of a user by adopting a configuration which includes both of the correction detectors 13 and 14.

As used herein, the following directional terms "forward, rearward, above, downward, vertical, horizontal, below, transverse, row and column" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. A radiation inspection apparatus comprising:
   a radiation source that irradiates linear radiation, which is parallel to an inspection direction set on an inspection target, to the inspection target;
   a line type detector that detects the radiation transmitted through the inspection target;
   a correction detector that is disposed in a position between the inspection target and the line type detector, the correction detector moving along the inspection direction to detect the radiation, which has been irradiated from the radiation source, at each of a plurality of inspection positions along the inspection direction; and
   a correction device that corrects the detection result of the line type detector by using the detection result of the correction detector, wherein
   the correction device comprises:
      a first calculation unit that obtains a first thickness of the inspection target at each inspection position in the inspection direction based on the detection result of the line type detector;
      a second calculation unit that obtains a second thickness of the inspection target at each inspection position in the inspection direction based on the detection result of the correction detector;
      a correction value calculating unit that obtains a correction value, which represents a difference between the first thicknesses of the inspection target obtained by the first calculation unit and the second thickness of the inspection target obtained by the second calculation unit, at each inspection position in the inspection direction; and
      a correction unit that corrects the first thickness of the inspection target, which has been obtained by the first calculation unit, by using the correction value, which has been obtained by the correction value calculating unit, at each inspection position in the inspection direction.

2. The radiation inspection apparatus according to claim 1, wherein
   the correction detector is disposed between the radiation source and the inspection target, and
   the correction device comprises a dividing unit that divides the detection result of the line type detector by the detection result of the correction detector at each inspection position in the inspection direction.

3. The radiation inspection apparatus according to claim 1, wherein
   the correction value calculating unit allows the thicknesses of the inspection target at the origin position obtained by the first and second calculation units to have the same value by using a difference between the thickness of the inspection target at a predetermined origin position in the inspection direction obtained by the first calculation unit and the thickness of the inspection target at the origin position obtained by the second calculation unit.

4. The radiation inspection apparatus according to claim 1, wherein
   the correction detector is disposed between the radiation source and the inspection target in addition to the position between the inspection target and the line type detector, and
   the correction device comprises a dividing unit that divides the detection result of the line type detector, which is used in the first calculation unit, by the detection result of the first correction detector, which is disposed between the radiation source and the inspection target, at each inspection position in the inspection direction, the dividing unit dividing the detection result of the second correction detector, which is disposed between the inspection target and the line type detector and is used in the second calculation unit, by the detection result of the first correction detector.

5. The radiation inspection apparatus according to claim 2, wherein
   the dividing unit normalizes the detection result of the line type detector by using a ratio between the detection results of the line type detector and the correction detector at the predetermined origin position in the inspection direction.

6. The radiation inspection apparatus according to claim 1, wherein
   the inspection direction is set so as to intersect a direction in which the inspection target is transported.

7. A radiation inspection apparatus comprising:
   a radiation source that is connected to a casing, the radiation source irradiating linear radiation, which is parallel to an inspection direction set on an inspection target, to the inspection target;
   a line type detector that is accommodated inside the casing, the line type detector including a plurality of detection elements arranged at constant intervals along the inspection direction, each of the detection elements detecting the radiation transmitted through the inspection target;
   a correction detector that is disposed in a position between the inspection target and the line type detector, the correction detector moving along the inspection direction to detect the radiation, which has been irradiated from the radiation source, at each of a plurality of inspection positions along the inspection direction; and
   a correction device that corrects the detection result of the line type detector by using the detection result of the correction detector, wherein the correction device comprises:
- a first calculation unit that obtains a first thickness of the inspection target at each inspection position in the inspection direction based on the detection result of the line type detector;
- a second calculation unit that obtains a second thickness of the inspection target at each inspection position in the inspection direction based on the detection result of the correction detector;
- a correction value calculating unit that obtains a correction value, which represents a difference between the first thicknesses of the inspection target obtained by the first calculation unit and the second thickness of the inspection target obtained by the second calculation unit, at each inspection position in the inspection direction: and
- a correction unit that corrects the first thickness of the inspection target, which has been obtained by the first calculation unit, by using the correction value, which has been obtained by the correction value calculating unit, at each inspection position in the inspection direction.

8. The radiation inspection apparatus according to claim 7, wherein
part of the plurality of detection elements is disposed at a position at which the radiation, which is irradiated from the radiation source and is not transmitted through the inspection target, is received.

9. The radiation inspection apparatus according to claim 7, wherein
the correction detector is disposed between the radiation source and the inspection target, and
the correction device comprises a dividing unit that divides the detection result of the line type detector by the detection result of the correction detector at each inspection position in the inspection direction.

10. The radiation inspection apparatus according to claim 7, wherein
the correction detector is disposed between the inspection target and the line type detector, and
the correction device comprises:
- a first calculation unit that obtains a thickness of the inspection target at each inspection position in the inspection direction based on the detection result of the line type detector;
- a second calculation unit that obtains a thickness of the inspection target at each inspection position in the inspection direction based on the detection result of the correction detector;
- a correction value calculating unit that obtains a correction value, which represents a difference between the thicknesses of the inspection target obtained by the first and second calculation units, at each inspection position in the inspection direction; and
- a correction unit that corrects the thickness of the inspection target, which has been obtained by the first calculation unit, by using the correction value, which has been obtained by the correction value calculating unit, at each inspection position in the inspection direction.

11. The radiation inspection apparatus according to claim 10, wherein
the correction value calculating unit allows the thicknesses of the inspection target at the origin position obtained by the first and second calculation units to have the same value by using a difference between the thickness of the inspection target at a predetermined origin position in the inspection direction obtained by the first calculation unit and the thickness of the inspection target at the origin position obtained by the second calculation unit.

12. The radiation inspection apparatus according to claim 10, wherein
the correction detector is disposed between the radiation source and the inspection target in addition to the position between the inspection target and the line type detector, and
the correction device comprises a dividing unit that divides the detection result of the line type detector, which is used in the first calculation unit, by the detection result of the first correction detector, which is disposed between the radiation source and the inspection target, at each inspection position in the inspection direction, the dividing unit dividing the detection result of the second correction detector, which is disposed between the inspection target and the line type detector and is used in the second calculation unit, by the detection result of the first correction detector.

13. The radiation inspection apparatus according to claim 9, wherein
the dividing unit normalizes the detection result of the line type detector by using a ratio between the detection results of the line type detector and the correction detector at the predetermined origin position in the inspection direction.

14. The radiation inspection apparatus according to claim 7, wherein
the inspection direction is set so as to intersect a direction in which the inspection target is transported.

15. A radiation inspection method comprising:
- a first step of irradiating linear radiation, which is parallel to an inspection direction set on an inspection target, to the inspection target;
- a second step of detecting the radiation transmitted through the inspection target;
- a third step of detecting the irradiated radiation at each of a plurality of inspection positions along the inspection direction; and
- a fourth step of correcting the detection result of the second step by using the detection result of the third step, wherein
the detecting the irradiated radiation at each of the plurality of inspection positions along the inspection direction is by a correction detector disposed between the inspection target and a line type detector configured to detect the radiation transmitted through the inspection target, and
the correcting the detection result is by a correction device, the correction device comprising:
- a first calculation unit that obtains a first thickness of the inspection target at each inspection position in the inspection direction based on the detection result of the line type detector;
- a second calculation unit that obtains a second thickness of the inspection target at each inspection position in the inspection direction based on the detection result of the correction detector;
- a correction value calculating unit that obtains a correction value, which represents a difference between the first thicknesses of the inspection target obtained by the first calculation unit and the second thickness of the inspection target obtained by the second calculation unit, at each inspection position in the inspection direction; and
- a correction unit that corrects the first thickness of the inspection target, which has been obtained by the first calculation unit, by using the correction value, which has been obtained by the correction value calculating unit, at each inspection position in the inspection direction.

16. The radiation inspection method according to claim 15, further comprising:
a fifth step of dividing the detection result of the second step by the detection result of the third step at each of the plurality of inspection positions in the inspection direction.

17. The radiation inspection method according to claim 15, further comprising:
a sixth step of obtaining a thickness of the inspection target at each inspection position in the inspection direction based on the detection result of the second step;
a seventh step of obtaining a thickness of the inspection target at each inspection position in the inspection direction based on the detection result of the third step;
an eighth step of obtaining a correction value, which represents a difference between the thicknesses of the inspection target obtained in the sixth step and the seventh step, at each inspection position in the inspection direction; and
a ninth step of correcting the thickness of the inspection target, which has been obtained in the sixth step, by using the correction value, which has been obtained in the eighth step, at each inspection position in the inspection direction.

18. The radiation inspection method according to claim 17, wherein
in the eighth step, the thicknesses of the inspection target at the origin position obtained in the sixth step and the seventh step are made to be the same as each other by using a difference between the thickness of the inspection target at a predetermined origin position in the inspection direction obtained in the sixth step and the thickness of the inspection target at the origin position obtained in the seventh step.

19. The radiation inspection method according to claim 16, wherein
in the fifth step, the detection result of the second step is normalized by using a ratio between the detection results of the second step and the third step at the predetermined origin position in the inspection direction.

* * * * *